United States Patent [19]

Ender

[11] Patent Number: 4,549,537

[45] Date of Patent: Oct. 29, 1985

[54] SPLINT FOR REDUCING AND MAINTAINING MOTIONLESS FRACTURES OF FINGERS AND THE METACARPUS AND PROCESS FOR PRODUCING SUCH A SPLINT

[76] Inventor: Hans G. Ender, Ferstelgasse 6/20, A-1090 Vienna, Austria

[21] Appl. No.: 255,318

[22] Filed: Apr. 17, 1981

[30] Foreign Application Priority Data

Apr. 25, 1980 [AT] Austria ................... 2252/80

[51] Int. Cl.$^4$ ............................................. A61F 5/04
[52] U.S. Cl. ................... 128/87 A; 128/89 R
[58] Field of Search ............... 128/87 R, 87 A, 89 R, 128/77, 90, 83, 85

[56] References Cited

U.S. PATENT DOCUMENTS

| 471,252 | 3/1892 | Hanley | 128/87 R |
|---|---|---|---|
| 3,943,923 | 3/1976 | Scheinberg | 128/89 R |
| 4,143,653 | 3/1979 | Wichman | 128/89 R |

FOREIGN PATENT DOCUMENTS

| 2599 | 3/1891 | United Kingdom | 128/89 R |

OTHER PUBLICATIONS

Orthopedic Equipment Co. Catalogue, Mar. 1975, p. 171, "Easter Finger Splint".

*Primary Examiner*—John D. Yasko
*Attorney, Agent, or Firm*—Holman & Stern

[57] ABSTRACT

A splint for reducing and maintaining in motionless position fractures of fingers and the metacarpus. The splint is designed such that it can be adapted in an optimum manner to the position of the broken finger assuming its intermediate bent position. For this purpose, the splint comprises a flat elongated base strip of plastically deformable material, said strip being movable in perpendicular direction to its plane, said strip being twistable around its longitudinal axis and said strip being shaped at its both opposing longitudinal edges such that the strip can also be bent within the plane of the strip. The splint has at least one transverse member being fixedly connected to the base strip at one end portion thereof and being, for the purpose of fixing the splint, bendable around the fore-arm in a direction perpendicular to its surface. The splint is provided with an envelope of resilient material.

15 Claims, 5 Drawing Figures

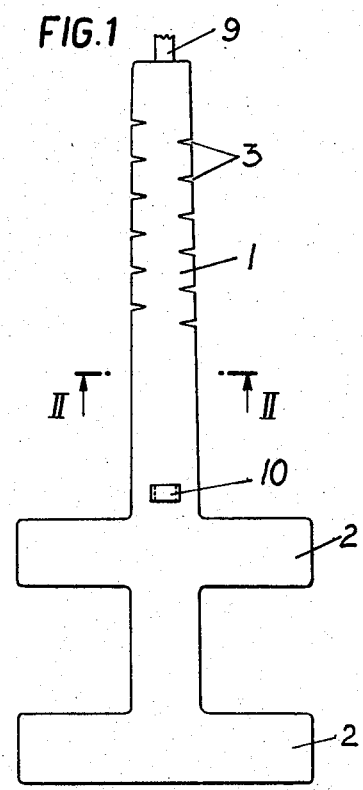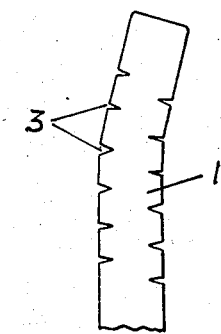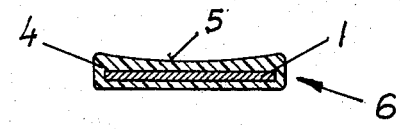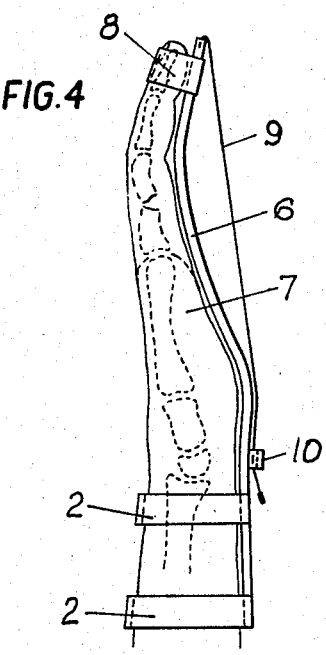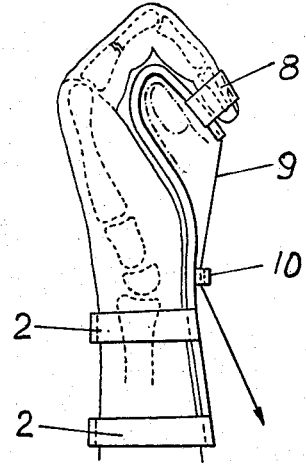

SPLINT FOR REDUCING AND MAINTAINING MOTIONLESS FRACTURES OF FINGERS AND THE METACARPUS AND PROCESS FOR PRODUCING SUCH A SPLINT

BACKGROUND OF THE INVENTION

The invention refers to a splint for reducing and maintaining motionless fractures of fingers and the metacarpus. The term "finger" as used herein includes the terminating members of a hand, including the thumb.

Such splints have long been used in accident surgery. The splints must be adapted to the fractured finger and the fractured metacarpus, respectively, and must maintain the adapted shape for unobjectionably supporting the fracture. Such adapting of splints is, however, difficult because the fingers extend in mutually parallel relation only in stretched position, whereas in bent position of the fingers the now curved axes of the fingers are, starting from a transversely extending hand vault, no longer parallelly arranged as in stretched position but are directed all to one single point approximately located at the scaphoid bone hump or at the area of the thumb ball. The axes of the fingers are thus gradually changing their position during a bending movement, starting from a parallel position corresponding to the stretched position of the fingers, until the axes of the fingers are essentially intersecting in one point with completely bent fingers. Fingers showing a fracture can, however, not be maintained motionless while being in stretched position. Instead, the fingers must maintained motionless while in an intermediate bent position of the fingers so that the sinews are stretched and the fingers will not become stiffened. As a consequence, the splint must be brought to a position corresponding to the intermediate bent position of the finger to be supported and the splint must maintain this position during the total healing process. This is not possible with known splints. Such splints can either not be bent into the position for correctly supporting the fractured finger in its intermediate bent position in an optimum manner or can not maintain the shape adapted to the finger as is required for successful healing. This is, for example, the case if the splint consists of a wire rack.

SUMMARY OF THE INVENTION

It is an object of the present invention to provide a new splint which will reliably support in an optimum manner the fractured finger and the fractured metacarpus, respectively, during the whole healing process.

It is a further object of the invention to provide a splint which can in a simple manner be bent into a position as is required for supporting the fractured finger and the fractured metacarpus, respectively, and which maintains in an optimum manner this position during the whole healing process.

It is a further object of the invention to provide a splint which, when used, does not require twisting the fractured finger and the fractured metacarpus, respectively, in an undesired manner.

These objects and still further objects of the invention become obvious when considering the description of the invention with reference to the drawings.

BRIEF DESCRIPTION OF THE DRAWINGS

FIG. 1 is a top plan view of a splint according to the invention, the envelope of resilient material being however omitted.

FIG. 2 is a section along line II—II of FIG. 1 and showing the envelope of resilient material.

FIG. 3 shows the upper end of the base strip forming part of the splint after having been bent.

FIG. 4 illustrates application of the splint according to the invention to a fractured finger still being in its essentially stretched position.

FIG. 5 shows the arrangement of the splint with the finger assuming its intermediate bent position in which the fracture must heal.

DETAILED DESCRIPTION OF THE INVENTION

As can be derived from the drawing, the splint comprises an elongated base strip 1 of plastically deformable material, preferably a metal sheet, for example an aluminum sheet, transmissive for X-rays and further comprises two transverse members 2 which, in the embodiment shown, form one single part with the base strip 1 but which can also be separately manufactured and can subsequently be connected with the base strip 1 by means of an adhesive, by rivetting or by welding. The base strip 1 is flat in its original condition. The transverse members 2 serve the purpose of fixing the splint on the wrist with one of its ends by bending the transverse members 2 around said wrist.

For reducing the fractured area and for keeping the finger motionless in the correct position, the splint must be bent into a definite position in a manner to be further described. Splints known up till now only could be twisted around their longitudinal axis or only be bent such that the longitudinal axis is brought from a straight line into a curved line. Both twisting and, bending the splint are, however, not sufficient to bring the splint into a position for supporting the finger in an optimum manner in its correct position. The build of the hand and of the fingers is such that the hand forms a longitudinal vault and a transverse vault. The longitudinal vault provides in connection with the finger-joints the possibility for the hand to grasp a cylindrical object, for example. The transverse vault also shapes the hand in a transverse direction and adds the possibility of moving the hand in a further dimension so that a sphere, for example, can be grasped or embraced by the hand. For this reason, the finger are of such construction that their axes are in essentially parallel relation in stretched position and that with the fingers assuming bent position the axes of the fingers now representing a curve are no longer mutually parallel. With the fingers finally assuming a completely bent position all axes are directed to a point approximately located at the thumb ball. If a splint is to support a finger assuming its bent position in an optimum manner and if twisting errors are to be excluded at the area of the fracture, the possibility of known splints to twist and to bend are insufficient for this purpose. In a splint according to the invention, the base strip 1 is provided at its both longitudinal edges with gaps 3 having the shape of gores and being delimited by straight lines. In place of the gaps having the shape of gores as shown, gaps being delimited by an arc of a circle or another curve also can be provided. These gaps 3 provide the possibility of bending the splint, as is shown in FIG. 3, in a transverse direction and within the plane of the splint. The gaps 3 thus provide the possibility to bend and twist, respectively, the splint in three different directions, so that the splint can be brought into any desired position and the reduced finger can be supported in an optimum manner in an optimum reduced position.

As can be seen from FIG. 2, the base strip 1 is surrounded as a whole by a cover or envelope 4 of resilient and yielding material, for example of synthetic plastic material, preferably polyurethane foam. For this purpose the base strip 1 previously manufactured by a punching operation is put into a mold and a polyurethane-forming material is poured or injected into the mold after it is closed. The mold is conveniently designed such that a depression 5 for accommodating the finger is formed at one side of the splint thus improving supporting action for the finger. An envelope of textile materials can, however, also be used.

For a broken finger to reduced and be maintained in motionless position by means of a splint according to the invention, the splint 6 is first fixed with its both transverse members 2 on the wrist of the respective hand and bent into a shape as shown in FIG. 4. Subsequently, the finger 7 is fixed at its tip by means of an adhesive tape 8 or the like, to the upper end of the splint. A fixing means 9, which can consist of wire or of a strip material, is fixed to this upper end of the splint. The fixing means 9 can be fixed either by embedding the end of the wire or strip material (preferably after previously securing the wire or strip material to the upper end of the base strip 1) into the envelope 4 consisting of synthetic plastic material during casting operation or by suspending the fixing means 9 within a recess, an eye or the like, provided at the upper end of the splint 6. Finally, a self-adhesive tape can be used which is fixed to the splint 6 by glueing operation.

The other end of the fixing means 9 is conveniently passed through a bushing 10 or the like, so that, when exerting a pulling force to this end of the fixing means 9, the splint 6 will become bent.

For reducing the fracture, the finger of the surgeon is pressed against the base-joint of the finger to be reduced and the finger is bent in downward direction. Thus, by the tension force resulting therefrom, the fracture, (which forms an angle opening to the stretch side at any rate above all if the base member of the finger is fractured), is brought into correct position, i.e. both parts of the broken member are bent backward into straight position. In this case it is essential that the broken finger is bent into a very definite position in which both parts of the fractured member assume its straight position. To provide the possibility of exactly and gradually bending the finger for reducing purposes, a pulling force can be exerted on the free end of the fixing means 9 until the broken member assumes its reduced position. In view of the finger being fixed to the splint 6 by means of the adhesive tape 8, the finger follows this movement of the splint. Simultaneously, the splint 6 is also brought into such a position that the finger now assuming the bent position shown in FIG. 5 points to the hump of the scaphoid bone. The finger thus is brought into an ideal position in which the fractured area is not subjected to torsion.

The tape forming the fixing means is conveniently provided with a serration on its end extending through the bushing 10, the teeth of which are slanted at one side so that the teeth can pass the bushing 10 when exerting a pulling force in one direction and the tape is arrested and maintained in its respective position when effecting a tension force in the opposite direction. Such self-arresting clamping devices are already known. By such an arrangement, the splint, together with the finger fixed thereon, is maintained in a bent position and the splint can not be backwardly bent without previously loosening the fixing means.

Of course, the fixing means also can be fixed at the area of the lower end of the splint in another manner, for example, by using the already mentioned self-adhesive tape to be fixed to the splint 6 or by winding a fixing means having the shape of a wire around the bushing 10 forming a protrusion.

The splint according to the invention can also be manufactured in a simple manner. According to an inventive process for producing the splint, the base strip 1 is together with its transverse members 2 and the weakening areas or, respectively, gaps 3 formed, by a punching operation from a metal sheet and then put into a mold whereupon the mold is closed and is filled with synthetic plastic material by pouring or injection. According to another inventive process for producing the splint, first the base strip 1 is formed together with its transverse members 2 and the weakening areas or, respectively, gaps 3, for example by punching operation from a metal sheet and subsequently put between two layers of the material, preferably textile material, forming the envelope. Both layers are mutually connected one to the other at the margin of the strip and the excessive portion of the material forming the envelope is severed in correspondence with the shape of the splint.

What is claimed is:

1. A splint for reducing and for maintaining in motionless position fractures of fingers and the metacarpus comprising:
    a flat elongated base strip of plastically deformable material, said strip being movable in perpendicular direction to its plane, said strip being twistable around its longitudinal axis and said strip being provided on both opposing longitudinal edges with gaps such that is can be transversely bent in its own plane,
    and at least one transverse member being fixedly connected at one end portion of the base strip and being adapted to be bent in a direction perpendicular to its surface around the fore-arm for fixing the splint.

2. A splint as claimed in claim 1 wherein the gaps are formed of gores delimited by straight lines.

3. A splint as claimed in claim 1 wherein the gaps are delimited by curves.

4. A splint as claimed in claim 1 wherein the base strip and the transverse members are provided with an envelope of resilient material.

5. A splint as claimed in claim 4 wherein the envelope is formed of a deformable synthetic plastic material.

6. A splint as claimed in claim 1 wherein the fixing means consists of a material having the shape of a wire, of a strip or of a tape.

7. A splint as claimed in claim 1 wherein the fixing means consists of a self-adhesive tape being glued to the forward end portion of the splint and to the end portion having fixed thereto the transverse members.

8. A splint as claimed in claim 1 wherein the fixing means is provided with a self-arresting clamping device on at least one end.

9. Process for producing a splint for reducing and maintaining in motionless position fractures of fingers and the metacarpus, as claimed in claim 1 comprising the steps:

producing a base strip together with its transverse members and the gaps from a metal sheet by a punching operation;

subsequently placing this punched part into a mold corresponding in shape to the splint and consisting of at least two mold parts;

introducing synthetic plastic material into the mold cavity after closing the mold or immediately prior to closing the mold;

allowing the synthetic plastic material to cure.

10. Process for producing a splint for reducing and maintaining in motionless position fractures of fingers and the metacarpus, as claimed in claim 1 comprising the steps:

producing a base strip together with its transverse members and the gaps from a metal sheet by a punching operation;

subsequently placing the punched part so produced between two layers of material forming the envelope;

connecting both layers at their marginal areas protruding over the punched part produced; and removing the excessive portion of the material forming the envelope in correspondence with the shape of the splint.

11. The process of claim 10 wherein the layers of material are textile material and are connected by gluing.

12. A splint for reducing and for maintaining in motionless position fractures of fingers and the metacarpus comprising:

a flat elongated base strip of plastically deformable material, said strip being movable in perpendicular direction to its plane, said strip being twistable around its longitudinal axis and said strip being provided on both opposing longitudinal edges with gaps such that it can be bent transversely in its own plane, at least one transverse member being fixedly connected at one end portion of the base strip and being adapted to be bent in a direction perpendicular to its surface around the fore-arm for fixing the splint, and a fixing means which mutually connects the forward portion of the bent splint with the end portion having fixed thereon the transverse members, means being provided for adapting the fixing means to the required length.

13. Process for producing a splint for reducing and maintaining in motionless position fractures of fingers and the metacarpus, as claimed in claim 1 comprising the steps:

producing a base strip together with its transverse members and the gaps from a metal sheet by a punching operation;

subsequently placing this punched part into a mold corresponding in shape to the splint and consisting of at least two mold parts;

introducing synthetic plastic material into the mold cavity after closing the mold or immediately prior to closing the mold;

allowing the synthetic plastic material to cure.

14. Process for producing a splint for reducing and maintaining in motionless position fractures of fingers and the metacarpus as claimed in claim 12, comprising the steps:

producing a base strip together with its transverse members and the gaps from a metal sheet by a punching operation;

subsequently placing the punched part so produced between two layers of material forming the envelope;

connecting both layers at their marginal areas protruding over the punched part produced; and removing the excessive portion of the material forming the envelope in correspondence with the shape of the splint.

15. The process of claim 14 wherein the layers of material are textile material and are connected by gluing.

* * * * *